United States Patent
Wachs et al.

(10) Patent No.: US 7,437,247 B2
(45) Date of Patent: Oct. 14, 2008

(54) METHOD OF DETERMINING PARAFFINIC CRUDE FLOW RESTART CONDITIONS

(75) Inventors: Anthony Wachs, Suresnes (FR); Françoise Brucy, Sevres (FR); Isabelle Henaut, Rueil Malmaison (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 114 days.

(21) Appl. No.: 11/296,278

(22) Filed: Dec. 8, 2005

(65) Prior Publication Data

US 2006/0130563 A1 Jun. 22, 2006

(30) Foreign Application Priority Data

Dec. 13, 2004 (FR) .................................. 04 13303

(51) Int. Cl.
*G01V 13/00* (2006.01)
(52) U.S. Cl. .......................................... 702/12; 702/13
(58) Field of Classification Search .................. 702/12, 702/13
See application file for complete search history.

(56) References Cited

U.S. PATENT DOCUMENTS

| 3,791,395 | A | * | 2/1974 | Dunlap et al. .................. 137/13 |
| 3,977,234 | A | | 8/1976 | Lynch et al. |
| 5,877,409 | A | | 3/1999 | Girling |
| 6,629,451 | B1 | | 10/2003 | Taylor |

FOREIGN PATENT DOCUMENTS

| FR | 2758185 | 7/1998 |
| FR | 2796152 | 1/2001 |

OTHER PUBLICATIONS

Cawkwell, M.G., and Charles, M.E., "An Improved Model for Start-Up of Pipelines containing Gelled Crude Oil", Journal of Pipelines, vol. 7 (1987), pp. 41-52.*
Houska, M. et al. "Start-Up of Celled Crude Oil Pipelines" Journal of Pipelines, vol. 6 (1987) pp. 15-24.*
Smith, Peter and Ramsden, Rex "The Prediction of Oil Gelation in Submarine Pipelines and the Pressure Required for Restarting Flow" 1978 European Offshore Petroleum Conference & Exhibition, pp. 283-290.*
Perkins, T.K. and Turner, J.B. "Starting Behavior of Gathering Lines and Pipelines filled with Gelled Prudhoe Bay Oil", 45th Annual SPE of AIME Fall Meeting, SPE-2997, Mar. 1971, pp. 301-308.*
Cooper, D.F. et al. "Transient Temperature Effects in Predicting Start-Up Characteristics of Gelling-Type Crude Oils" International Conference of Heat Transfer vol. 4, 1978, pp. 67-71.*

* cited by examiner

*Primary Examiner*—Michael Cygan
(74) *Attorney, Agent, or Firm*—Antonelli, Terry, Stout & Kraus, LLP.

(57) ABSTRACT

The invention relates to a method of estimating the flow restart conditions of a paraffinic hydrocarbon in a pipe, wherein the following stages are carried out:
selecting a theological model,
determining the temperature and shear stress fields in the steady hydrocarbon flow,
evaluating the conductive thermal exchanges during circulation standstill phases, from the steady flow temperatures and the standstill time taken into account,
selecting various sections of the pipe and recording the thermomechanical scenarios undergone by the hydrocarbon in these sections,
experimentally measuring the rheological parameters of the model on a sample of the hydrocarbon, according to each one of said scenarios, and taking into account these experimental measurements to evaluate the value of the pressure that restarts circulation of the paraffinic hydrocarbon in the pipe.

6 Claims, 2 Drawing Sheets

METHOD OF DETERMINING PARAFFINIC CRUDE FLOW RESTART CONDITIONS

FIELD OF THE INVENTION

The present invention relates to the sphere of hydrocarbon pipe transportation for oil reservoirs development.

BACKGROUND OF THE INVENTION

In the case of paraffinic type crude oils, operators have to face the risk of a circulation standstill in the pipe which may lead, depending notably on the time of standstill and on unfavourable temperature conditions, to a certain "solidification" or gelification of the crude in the pipe. In this case, it is clear that the circulation restart conditions can lead to pressures that are extremely delicate to control with local installations. In order to prevent or limit this restart difficulty risk, one may be led to empty the pipes of the paraffinic hydrocarbons and to replace them by simple fluids. This operation involves a considerable production time waste.

One may also be led to dimension the pipes or to provide thermal insulation and/or heating of the pipes so as to increase the time available for a circulation standstill.

Current restart pressure estimations can lead to pointless investment in emptying, pumping pipe, thermal insulation, heating installations, and/or to perform pointless emptying (when possible). It can be noted that, generally, a production pipe can rarely be emptied. This is possible for a planned circulation standstill, if adequate means are available, but it is more rarely possible in unpredictable cases.

The present invention provides a new method of determining the flow restart conditions of paraffinic crudes in pipes. This method both comprises experimental stages and numerical calculation stages.

SUMMARY OF THE INVENTION

The present invention relates to a method of estimating the flow restart conditions of a paraffinic hydrocarbon in a pipe, wherein the following stages are carried out:

a) selecting a rheological model suited to the nature of the paraffinic hydrocarbon, b) determining the temperature and shear stress fields in the steady hydrocarbon flow, along the axis of the pipe, c) evaluating the conductive thermal exchanges during circulation standstill phases, from the steady flow temperatures and the standstill times taken into account, d) selecting various sections of the pipe and recording the thermomechanical scenarios undergone by the hydrocarbon in these sections, e) experimentally measuring the Theological parameters of said model on a sample of said hydrocarbon, according to each one of said scenarios, and f) taking into account said experimental measurements to evaluate the value of the pressure that restarts circulation of the paraffinic hydrocarbon in the pipe.

According to the method, the Houska rheological model can be selected.

In stage b), determination of the temperature and shear stress fields in the steady flow in the pipe can be done preferably by one-dimensional calculations.

In stage d), sections can be selected in the static cooling zone and in the dynamic cooling zone.

The scenarios can comprise: the initial and final temperatures, the cooling rate, and the shear rate on steady flow.

The compressibility of the flowing hydrocarbon can be evaluated, and said compressibility evaluation can be carried out at the final temperature for the various scenarios.

In paraffinic crude flow restart surveys, the main questions can be:

What is the minimum restart pressure?

What is the time required to empty the pipe and to recover steady flow conditions?

The main problem concerns the complex behaviour of paraffinic crudes: non-Newtonian thermodependent and thixotropic rheological properties, and compressibility.

The knowledge and experience accumulated by the applicant during the past few years allow some particular points to be underlined:

From an experimental point of view, it is important to have the capacity to characterize the crude from a rheological standpoint under conditions close to those encountered in the field. Thermal history data, mechanical history data, the standstill times notably have to be studied in order to provide parameters of the rheological model considered representative of the case studied, the importance of the initial state of the crude in the pipe upon flow restart. Thus, it is necessary to precisely describe the standstill phase to guarantee correct study of the restarting stage, from a numerical point of view, the mathematical difficulties linked with taking into account a thixotropic, thermodependent yield stress fluid in the simulation of a compressible flow with fluid/fluid interface have to be overcome.

BRIEF DESCRIPTION OF THE FIGURES

The new method provided can be described in 7 stages: experimental stages combined with numerical stages based on an analysis and complete comprehension of the standstill and restart phases. These stages are described in detail hereafter and illustrated by the accompanying figures wherein.

DETAILED DESCRIPTION

Figure 3:
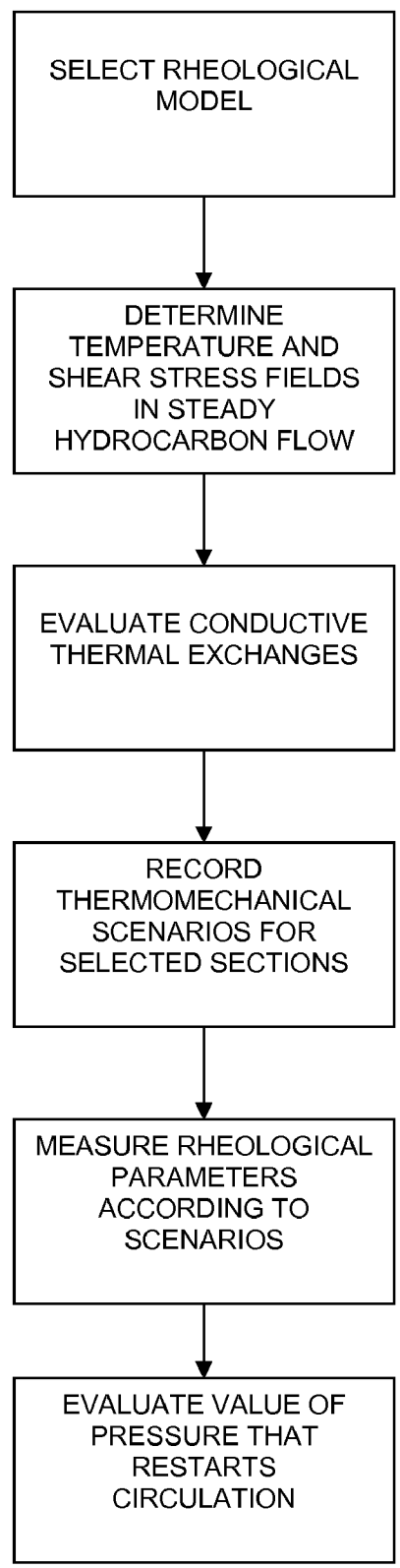
FIG. 3 is a flow chart showing the method of the present invention.

FIG. 3 is a flow chart showing the method of the present invention, including the following stages.

STAGE 1: Selection of the Rheological Model Describing the Crude and Determination of its Rheological Parameters Once the type of rheological model selected, the Theological parameters of the hydrocarbon in question are experimentally determined. These parameters are then used in the thermal calculations of stage 2.

In particular, a reliable and precise measuring technique has been developed for determination of the parameters of the Houska rheological model, defined by:

$$\tau = (\tau_{y0} + \lambda \tau_{y1})\frac{D}{\|D\|} + 2(k + \lambda \Delta k)\dot{\gamma}^n D \tag{1}$$

$$\frac{D\lambda}{Dt} = a(-\lambda) - b\lambda\dot{\gamma}^m \tag{2}$$

with:

$\tau$=stress tensor

D=deformation ratio tensor $\dot{\gamma}$=generalized shear rate
$\|.\|$=tensor norm
$D/Dt$=Lagrangian derivative and the Houska parameters are:
$\tau_{y,0}$=permanent yield stress
$\tau_{y,1}$=thixotropic yield stress
k=permanent viscosity
$\Delta k$=thixotropic viscosity
n=shear thinning index
a=gel regain parameter
b=gel destructuration parameter
m=destructuration rate adjustment parameter.

We consider that the Houska model, which corresponds to a generalized yield stress fluid model (equation (1)) coupled with an equation of a structure parameter (equation (2)) to describe the thixotropy, is the most suitable for describing the behaviour of paraffinic crudes. This model is therefore preferably used.

STAGE 2: Description of the Steady Flow

Figure 1:
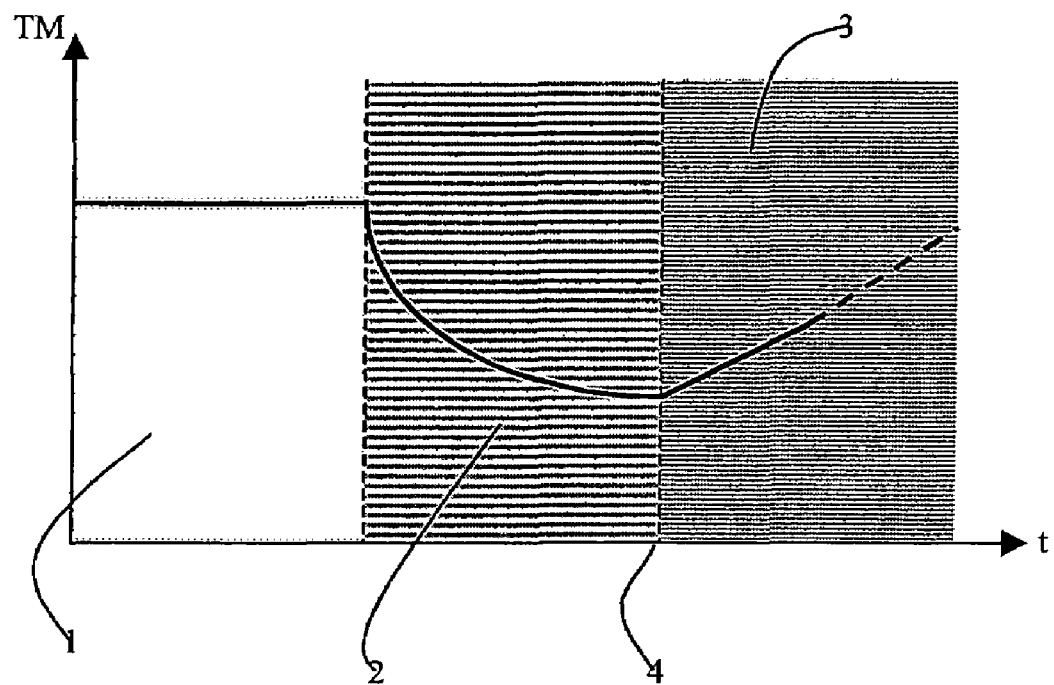
FIG. 1 illustrates the chronology of events in the pipe.

From a chronological point of view, precise description of the initial state of the crude in the pipe requires description of the standstill phase, which itself requires description of the steady flow, as illustrated in FIG. 1 which shows the evolution of the average temperature TM as a function of time t. Zone 1 corresponds to the steady flow, zone 2 to the flow standstill time, and zone 3 to restart. It is at point 4 that the initial state of the crude upon restart is considered. In order to take account of the complete thermomechanical history of the crude, the steady flow first has to be studied.

The profile of the temperature and shear stress fields on steady flow along the axis of the pipe is obtained by means of one and/or two-dimensional flow and thermal transfer calculations. These calculations correspond to the numerical simulation of a thermodependent yield stress fluid flow. The thermal convection and conduction during flow are taken into account in the energy equation. The temperature boundary conditions on the outer wall of the pipe are those of the field.

The two-dimensional calculations take account of the radial variations of all the physical quantities, notably the yield stress. These calculations are relatively long and are considered only for pipes of limited length. One-dimensional calculations are preferably carried out because they allow to consider conditions of any length.

STAGE 3: Thermal Calculations During the Standstill Phase

Figure 2:
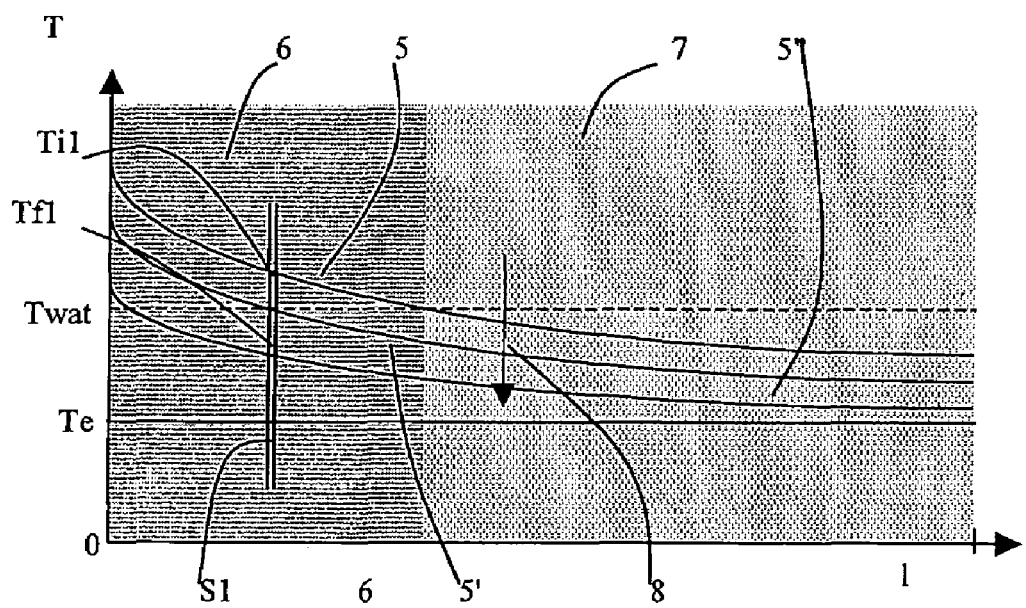
FIG. 2 shows cooling during the standstill phase.

Two-dimensional thermal calculations without flow are carried out in order to obtain the temperature evolution in the pipe during the standstill phase, as shown in FIG. 2. Only the conductive thermal exchanges are considered (natural convection, generally low in this case in the crude, is not taken into account). Again, the temperature boundary conditions on the outer wall of the pipe are those of the field.

FIG. 2 shows, as a function of length l of the pipe, the temperature curves of the crude in the pipe from circulation standstill. Te is the outside temperature, Twat the temperature of appearance of paraffin crystals. Curve 5 gives the temperature in the pipe as circulation is stopped, i.e. the temperature of the steady flow obtained in stage 2. Zone 6 where the temperature of the crude is, as circulation is stopped, higher than Twat is referred to as static cooling zone. Zone 7 where the temperature of the crude is already lower than Twat as circulation is stopped is a dynamic cooling zone. The other curves 5' and 5" show the evolution of the temperatures as a function of the standstill time, as shown by arrow 8.

STAGE 4: Selection of the Thermomechanical Scenarios

By means of the temperature profile evaluation calculations of stage 3, a certain number of sections (S1 for example) are selected at different points of the pipe, where the representative thermomechanical scenarios are taken into account (final temperature in the pipe (Tfl), cooling rate, static (Til) or dynamic cooling). The sections where the crude flows at a higher temperature than the temperature of appearance of paraffin crystals (Twat), and is then cooled to a temperature below Twat at rest, are representative of static cooling. The sections where the crude flows at a lower temperature than the temperature of appearance of paraffin crystals (Twat) (the crude is cooled while flowing) are representative of dynamic cooling.

STAGE 5: Experimental Characterization

Experimental characterization of the behaviour of the crude is carried out under the conditions described by the thermomechanical scenarios considered in each section selected. A fluid sample is sheared in a manner corresponding to the steady flow, at the initial temperature at standstill (Til for example). It is then cooled at the cooling rate corresponding to the scenario until the final temperature (Tfl) is reached. The rheological parameters of the Theological model selected are measured by means of this procedure. It guarantees that the rheological parameters are measured under conditions similar to the field conditions, over the total length of the pipe. On the other hand, the volume contraction of the crude once cooled to the final temperature is experimentally measured. This allows to evaluate the compressibility of the fluid, a parameter of the restart model.

STAGE 6: Description of the Initial State Upon Restart

As mentioned above, precise study of the restart phase is based on a reliable description of the state of the crude in the pipe, i.e. of the crude when flow restarts.

STAGE 7: 1D Restart Model

A numerical 1D restart model simulates the restart phase from an initial state of the crude in the pipe. The calculations are isothermal and model emptying of the pipe filled with gelled crude by injection of another fluid, for example an available fluid whose flow mode is close to the Newtonian flow (water, hot crude, gas oil, . . . ).

For an input pressure, the 1D model allows to determine whether the flow restarts or not. If it restarts, the times required for emptying the pipe and for recovering steady flow conditions are determined. Concerning the possibility of restarting or not, this means that, by dichotomy, by means of several calculations, the user can rapidly determine the minimum pressure required to restart the flow, whatever the initial state and without addition of any other equation (such as the relation $\Delta p = 4\tau_y L/D$, known to overestimate the restart pressure).

The 1D model takes account of all the characteristics of the isothermal problem: yield stress fluid, thixotropy, compressibility and fluid/fluid interface. 1D modelling allows to consider any pipe length. The topography of the formation on which the pipe lies is not taken into account in the model, but it can indirectly orient selection of the pipe sections in the stage (the points of the pipe at high altitude are generally synonymous with low outside temperatures and conversely).

The method according to the invention provides a coherent framework based on fine comprehension of the various phenomena that appear when stopping/restarting circulation in a pipeline filled with paraffinic crude, and it comprises experimental and numerical parts that interfere and combine. The final goal of the method is to provide a better estimation of the pressure and of the restart times.

The invention claimed is:

1. A method of estimating the flow restart conditions of a paraffinic hydrocarbon in a pipe, wherein the following stages are carried out:
   a) selecting a rheological model suited to the nature of the paraffinic hydrocarbon,
   b) determining the temperature and shear stress fields in the steady hydrocarbon flow, along the axis of the pipe,
   c) evaluating the conductive thermal exchanges during circulation standstills, from the steady flow temperatures and the standstill times taken into account,
   d) selecting various sections of the pipe and recording the thermomechanical scenarios undergone by the hydrocarbon in these sections, said scenarios including the initial and final temperatures, the cooling rate and the shear rate under steady circulation,
   e) experimentally measuring the rheological parameters of said model on a sample of said hydrocarbon, according to each one of said scenarios, and
   f) taking into account said experimental measurements to evaluate the value of the pressure that restarts circulation of the paraffinic hydrocarbon in the pipe.

2. A method as claimed in claim 1, wherein the Houska rheological model is selected.

3. A method as claimed in claim 1 wherein, in stage b), said fields are determined by one-dimensional calculations.

4. A method as claimed in claim 1 wherein, in stage d), sections are selected in the static cooling zone and in the dynamic cooling zone.

5. A method as claimed in claim 1, wherein the compressibility of the flowing hydrocarbon is evaluated.

6. A method as claimed in claim 5, wherein evaluation of the compressibility is done at the final temperature for the various scenarios.

* * * * *